United States Patent [19]

Kontos

[11] Patent Number: 5,439,445
[45] Date of Patent: Aug. 8, 1995

[54] SUPPORT CATHETER ASSEMBLY

[75] Inventor: Stavros B. Kontos, Woodcliff Lake, N.J.

[73] Assignee: Boston Scientific Corporation, Watertown, Mass.

[21] Appl. No.: 267,037

[22] Filed: Jun. 27, 1994

Related U.S. Application Data

[63] Continuation of Ser. No. 925,864, Aug. 7, 1992, abandoned.

[51] Int. Cl.⁶ ............................................. A61M 29/00
[52] U.S. Cl. ...................................... 604/96; 604/53; 604/95; 606/194
[58] Field of Search ..................... 604/96, 95, 53, 280, 604/281, 282, 283, 101–104; 606/191–194

[56] References Cited

U.S. PATENT DOCUMENTS

| | | |
|---|---|---|
| 3,605,750 | 9/1971 | Sheridan et al. |
| 4,183,102 | 1/1980 | Guiset . |
| 4,279,252 | 7/1981 | Martin . |
| 4,503,569 | 3/1985 | Dotter . |
| 4,509,523 | 4/1985 | Pevsner . |
| 4,581,017 | 4/1986 | Sahota . |
| 4,616,652 | 10/1986 | Simpson . |
| 4,762,129 | 8/1988 | Bonzel . |
| 4,820,271 | 4/1989 | Deutsch . |
| 4,824,435 | 4/1989 | Giesy et al. |
| 4,893,623 | 1/1990 | Rosenbluth . |
| 4,909,252 | 3/1990 | Goldberger . |
| 4,947,864 | 8/1990 | Shockey et al. |
| 4,976,691 | 12/1990 | Sahota . |
| 4,983,167 | 1/1991 | Sahota . |
| 4,988,356 | 1/1991 | Crittenden et al. |
| 5,000,734 | 3/1991 | Boussignac et al. |
| 5,000,743 | 3/1991 | Patel . |
| 5,002,531 | 3/1991 | Bonzel . |
| 5,019,042 | 5/1991 | Sahota . |
| 5,035,686 | 7/1991 | Crittenden et al. |
| 5,040,548 | 8/1991 | Yock . |
| 5,061,273 | 10/1991 | Yock . |
| 5,090,958 | 2/1992 | Sahota . |
| 5,108,370 | 4/1992 | Walinsky . |
| 5,131,407 | 7/1992 | Ischinger et al. |
| 5,143,093 | 9/1992 | Sahota . |
| 5,147,377 | 9/1992 | Sahota . |

(List continued on next page.)

FOREIGN PATENT DOCUMENTS

WO92/07606 5/1992
WO92/07610 5/1992 WIPO .

OTHER PUBLICATIONS

Matthew L. Carr, "The Use of the Guiding Catheter in Coronary Angioplasty: The Technique of Manipulating Catheters to ... Tight Coronary Stenoses," *Catheterization and Cardiovascular Diagnosis*, 12:189–197 (1986).

J. F. Reidy et al., "Transcatheter Occlusion of Coronary to Bronchial Anastomosis by Detachable Balloon Combined with Coronary Angioplasty at Same Procedure," *Br. Heart J.*, 49:284–7, 1983.

Little, "Probe Angioplasty of Total Coronary Occlusion Using an Intracoronary Probing Catheter ™", *Catheterization and Cardiovascular Diagnosis*, 17:218–223 (1989).

*Primary Examiner*—John D. Yasko
*Attorney, Agent, or Firm*—Fish & Richardson

[57] ABSTRACT

A support catheter assembly for facilitating medical procedures includes a tubular body and a continuous lumen from its proximal end to its distal end. A manipulating member is connected to the tubular body for inserting, advancing, withdrawing and maneuvering the body during a medical procedure. The manipulating member may be a wire or a manipulating tube. The tubular body also may be provided with a funnel shaped lumen opening at its proximal end to facilitate insertion of devices therethrough, and radiopaque markers for subcutaneously detecting the location of the device during a medical procedure and, more particularly, for detecting its location relative to other devices used in the medical procedure. A method also is disclosed for using the tube assembly to facilitate insertion of a PTCA catheter into a stenotic region and for holding open the lumen through that region after angioplasty has been performed.

33 Claims, 6 Drawing Sheets

U.S. PATENT DOCUMENTS

| | | |
|---|---|---|
| 5,160,321 | 11/1992 | Sahota . |
| 5,163,903 | 11/1992 | Crittenden et al. . |
| 5,181,911 | 1/1993 | Shturman . |
| 5,183,464 | 2/1993 | Dubrul et al. . |
| 5,190,058 | 3/1993 | Jones et al. . |
| 5,192,307 | 3/1993 | Wall . |
| 5,226,888 | 7/1993 | Arney . |
| 5,234,407 | 8/1993 | Teirstein et al. . |
| 5,255,690 | 10/1993 | Keith et al. . |
| 5,263,932 | 11/1993 | Jang . |
| 5,267,958 | 12/1993 | Buchbinder et al. . |
| 5,290,247 | 3/1994 | Crittenden . |
| 5,299,575 | 4/1994 | Sandridge . |
| 5,342,297 | 8/1994 | Jang . |

SUPPORT CATHETER ASSEMBLY

This is a continuation of application Ser. No. 07/925,864, filed Aug. 7, 1992, now abandoned.

BACKGROUND OF THE INVENTION

1. Field of the Invention

The present invention relates generally to a medical device and procedures for employing the device. More particularly, it relates to a support catheter assembly with particular utility in facilitating insertion of a PTCA balloon into a lesion. The present invention also has utility as a stent, for maintaining a continuous passage, e.g., through an area of an artery or vein which is otherwise susceptible to collapsing or restenosing.

2. Description of the Prior Art

PTCA catheters and percutaneous medical procedures for angioplasty are well known. In such procedures, a flexible PTCA catheter generally is percutaneously inserted into a blood vessel of a patient and guided through the patient's vascular system to the location of a restriction. Insertion and manipulation of the PTCA catheter is frequently facilitated by use of a guide catheter. However, often these guide catheters are not able to reach all the way to the restriction. Thus, the gap between the distal end of the guide catheter and the stenotic region to be opened must be traversed by the PTCA catheter alone.

As those skilled in the art know, the distal end of a PTCA catheter is made to be extremely soft and flexible so as to facilitate its passage through tortuosities and restrictions in the vascular system. This flexibility, however, also makes the catheter readily susceptible to kinking and bending. The guide catheter is employed, at least in part, to restrict the radial deflection of the PTCA catheter and thereby prevent buckling and kinking.

Figure 14:
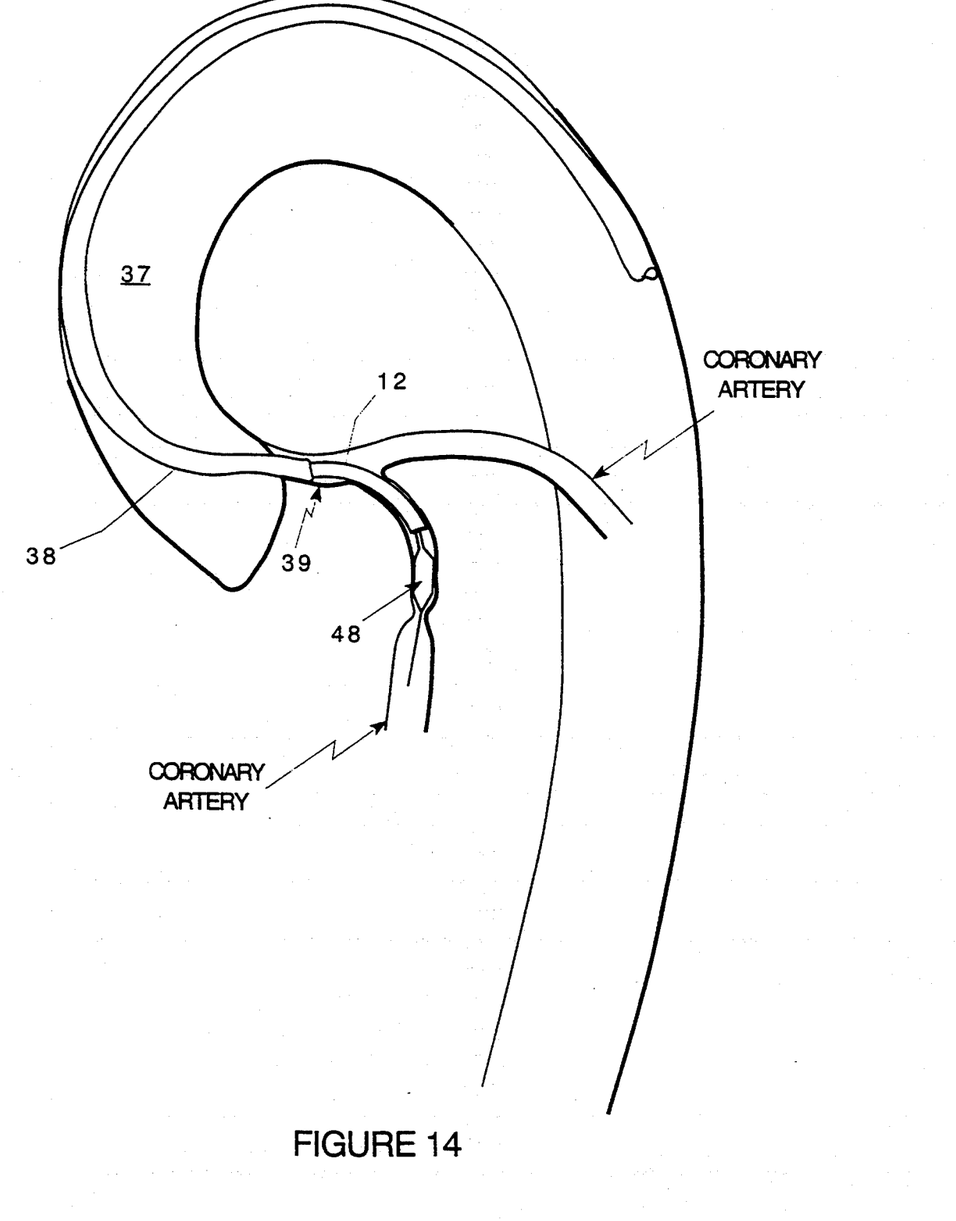
FIG. 14 is a schematic cross-sectional view of the aorta, the coronary ostia and two coronary arteries illustrating an angioplasty procedure employing a support catheter of the instant invention.

The guide catheter, however, can generally reach only to the coronary ostia, whereas the lesion to be opened is most commonly located in one of the coronary arteries leading from the ostia. Thus, the balloon catheter must negotiate the ostia, enter the coronary artery and pass through the coronary artery to the lesion without the help of the guide catheter (see FIG. 14). The instant invention may be used to facilitate the passage of the balloon catheter from the end of the guide catheter to the lesion.

Support structures for advancing and guiding a PTCA balloon catheter are well known. As discussed above, a guide catheter provides an independent support structure. Integral support structures also have been developed. For example, U.S. Pat. No. 4,762,129 (Bonzel) describes a dilation catheter which includes a balloon capable of being enlarged by injecting a fluid through an aspiration tube that terminates in the balloon. The aspiration tube is arranged laterally offset from a segment of flexible tube that forms a passage through the balloon for a guide wire. The aspiration tube, which is reinforced with a stabilizing wire, also serves to transmit thrust and tension forces to push and pull the balloon to and fro and rotate it on the guide wire.

Coronary arterial stenoses generally are caused by the accumulation of plaque on the artery wall. Angioplasty reduces the arterial restriction by expanding a balloon within the stenotic region and compressing the plaque against the vessel wall, thereby increasing the size of the lumen in that region. However, the plaque has a tendency to return to its original form and again close down or severely restrict the arterial lumen. This restenosing, if it occurs, may occur as quickly as within only a few minutes, although it may not occur for a few weeks, or even for several months. The tendency for restenosis is of particular concern where angioplasty is performed preparatory to surgery, when it is imperative that the passage through the artery be kept open, at least until the surgeon has had an opportunity to operate.

SUMMARY OF THE INVENTION

The present invention provides a support catheter, which can also function as a stent, connected to means such as a wire handle, to facilitate its insertion and manipulation. By use of such manipulating means, the support catheter can be inserted into and passed through a guide catheter, over a PTCA catheter, and out the distal end of the guide catheter so as to function as an extension of the guide catheter to bridge the gap (or at least some of it) between the end of the guide catheter and the stenosis to be opened. The present invention permits a physician to deliver, with greatly reduced risk of bending or kinking, a PTCA catheter to a site of coronary vessel restriction. It also facilitates the exchange of one catheter for a larger or smaller one. In addition, it provides a structure which can be inserted, after angioplasty, into a newly opened area of the lesion, thereby to prevent restenosis. Also, the support catheter of the instant invention can be made small enough to enter the coronary artery, something the guide catheter could not do.

In one embodiment of the present invention, the manipulating means is a wire attached to the proximal end of the support catheter.

In another embodiment of the present invention, the manipulating means is an extension tube. The extension tube is attached to the proximal end of the support catheter, and is provided with a longitudinally extending slit, e.g., for passing therethrough a guide wire or PTCA catheter tube. This structure provides direct access to the support catheter assembly at the proximal end of a guide catheter for fast insertion, withdrawal, or exchange of various balloon catheters.

BRIEF DESCRIPTION OF THE DRAWINGS

These and other features and advantages of the present invention readily will be apparent from the following detailed description read in conjunction with the accompanying drawings, wherein.

DETAILED DESCRIPTION OF THE PREFERRED EMBODIMENTS

Referring now to the drawings, wherein like reference numerals correspond to like or similar elements throughout, FIGS. 1 to 4 illustrate a support catheter assembly (hereinafter "support assembly") 10 of the present invention.

Figure 1:
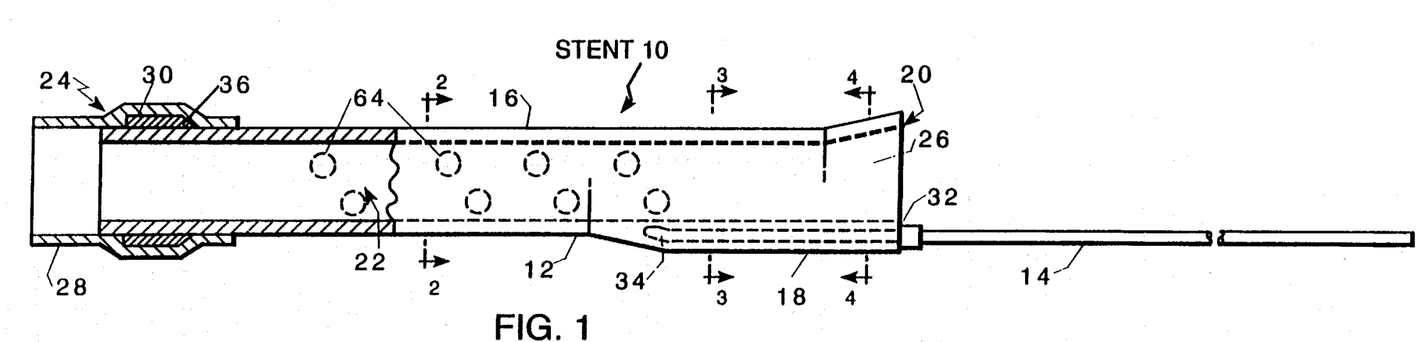
FIG. 1 is a side plan view of a support catheter of the present invention, cut-away in part to show in longitudinal cross-section a tubular body having a soft tip and radiopaque marker, and a manipulating wire.

Support assembly 10 is composed of two major elements, a body 12 and an insertion/manipulation wire 14. Body 12, which may be viewed as a mini guide catheter, includes a tube 16 having a base portion 18 at its proximal end 20. Tube 16 has a continuous lumen 22 therethrough from proximal end 20 to distal end 24. Body 12 also may include a funnel portion 26 formed at proximal end 20, and a soft tip 28 disposed at distal end 24. Wire 14 is attached to body 12 at base portion 18. Support assembly 10 also may include a distal marker band 30 and a proximal marker band 32.

Figure 2:
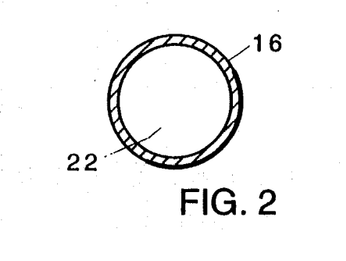
FIG. 2 is a cross-sectional view, taken along line 2—2 of FIG. 1, of one embodiment of a tubular body of the present invention.

As shown in FIGS. 1 to 4, tube 16 is generally cylindrical. More specifically, as shown in FIGS. 1 and 2, at distal end 24, tube 16 and lumen 22 are cylindrical and coaxial.

Figure 3:
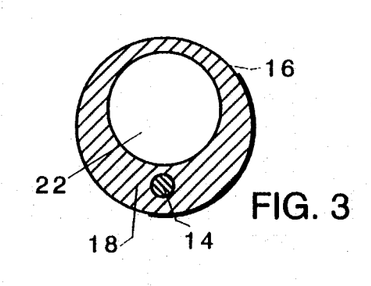
FIG. 3 is a cross-sectional view, taken along line 3—3 of FIG. 1, illustrating a base portion of the tubular body of one embodiment of the present invention.

As best shown in FIGS. 1 and 3, at proximal end 20, the outer wall of tube 16 is enlarged on one side (bottom side in FIGS. 1, 3 and 4) to form base portion 18, and may be flared out at proximal end 20 to form funnel portion 26. However, lumen 22 generally is continuous throughout.

It will be appreciated that the conical opening of lumen 22 at funnel portion 26 facilitates insertion of a PTCA catheter or the like therethrough.

Tube 16 may be composed of any pliable material suitable for percutaneous medical procedures, but preferably is composed of a molded plastic material, such as polyethylene.

Referring again to FIG. 1, soft tip 28 generally is cylindrical in shape and extends coaxially from distal end 24 of tube 16. Soft tip 28 may be composed of any highly flexible material suitable for percutaneous medical procedures, but preferably is composed of a soft plastic such as a copolymer of polyethylene and ethylvinylalcohol (EVA). It will be appreciated that a soft, flexible, pliable distal tip substantially reduces the risk of injury to a vessel wall, as well as of inadvertently dislodging portions of plaque from a lesion during manipulation of body 12.

Marker band 30, which is disposed at distal end 24, is preferably composed of a material that is detectable subcutaneously through the use of X-ray or fluoroscopy techniques, i.e., it is preferably radiopaque. As shown in FIG. 1, marker band 30 may be retained between soft tip 28 and tube 16 within recess 36. Of course, numerous other methods for disposing marker band 30 at distal end 24 will be readily apparent to those skilled in the art.

Figure 4:
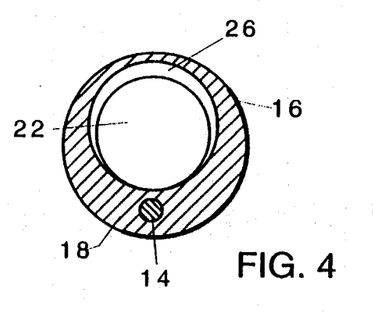
FIG. 4 is a cross-sectional view, taken along line 4—4 of FIG. 1, illustrating a funnel opening of the base portion of one embodiment of the present invention.

Insertion wire 14 is attached to base portion 18 at proximal end 20 of tube 16, and preferably is permanently affixed thereto. For example, as best shown in FIGS. 1, 3 and 4, wire 14 may be connected to base portion 18 by inserting it into a receiving hole 34, and affixing it therein by, for example, gluing, pressure fitting, shrink fitting, or the like. Alternatively, tube 16 may be molded directly onto application wire 14. Numerous other methods of connecting wire 14 to body 12 will readily occur to those skilled in the art. It will be appreciated that this configuration, wherein tube 16 has an eccentric cross-section at base portion 18 and wire 14 is affixed thereto, provides leverage for facilitating manipulation of body 12.

As shown in FIG. 1, a marker band 32 also may be disposed at the proximal end of bridge tube 16, e.g., on manipulating wire 14 adjacent base portion 18, and preferably is affixed thereto, e.g., by brazing or crimping. Marker band 32 also is preferably composed of a material that is detectable subcutaneously, and most preferably is radiopaque.

The size and shape of the various elements of support assembly 10 may vary depending on the desired application. In the application depicted in FIGS. 1 to 4, tube 16 has a 0.055 inch outer diameter and lumen 22 has a 0.045 inch diameter. (See, e.g., FIG. 2). At base portion 18, body 12 has a 0.065 inch outer diameter. (See, e.g., FIG. 3). Body 12 is approximately 1 foot in length including approximately 1 inch of base portion 18 and approximately 0.1 inch of funnel portion 26. Soft tip 28 is arranged to extend coaxially from distal end 24 for about 0.08 inch, and marker band 30 is approximately 0.055 inch inner diameter by 0.060 inch outer diameter by 0.080 inch long. Wire 14 is 0.020 inch diameter stainless steel, and is generally at least about 50 inches long and preferably about 53 inches long (See, e.g., FIGS. 1 and 4.) These sizes generally are suitable for existing PTCA catheters, such as the INTEGRA ™ catheter marketed by Datascope Corp., the assignee of the present invention. Of course, other sizes may be used for other applications.

Figure 5:
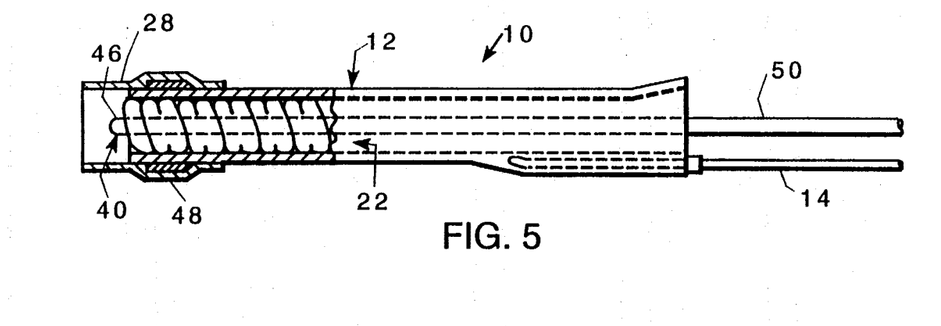
FIG. 5 is a side schematic view of a support catheter of the present invention having a PTCA catheter disposed therein.

As noted, these sizes may vary depending upon the application to which the device is to be put. When it is to be used with a PTCA catheter, lumen 22 should be at least large enough to permit passage therethrough of the deflated PTCA balloon. For example, FIG. 5 is a side schematic view of the support assembly 10 of FIGS. 1 to 4 and a PTCA catheter 40, with the deflated balloon 48 resident in lumen 22 thereof. It is also believed to be preferable for body 12 to be at least long enough for the entire PTCA balloon 48 to fit therein, although a somewhat longer body, perhaps about 8 times as long as the balloon 48 is believed most desirable.

Figure 6A:
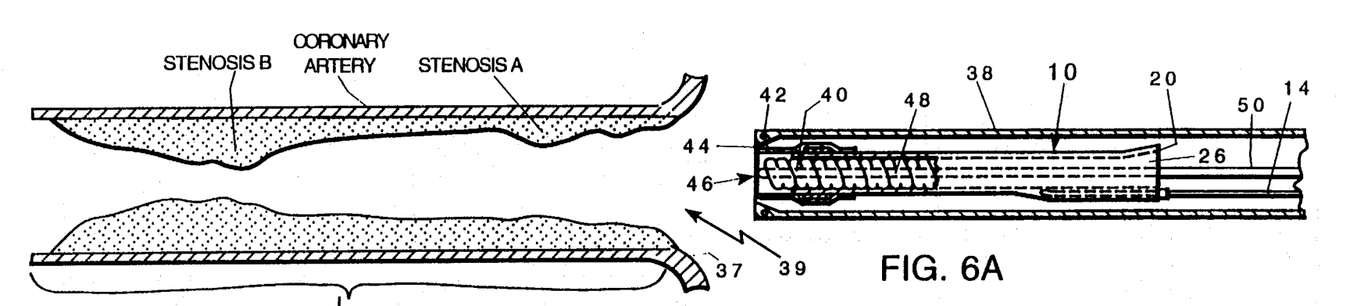
FIGS. 6A to 6C are cross-sectional views showing schematically three stages in a process for guiding a PTCA catheter to a coronary artery lesion employing a support catheter according to the present invention.
Figures 6B, 6C:
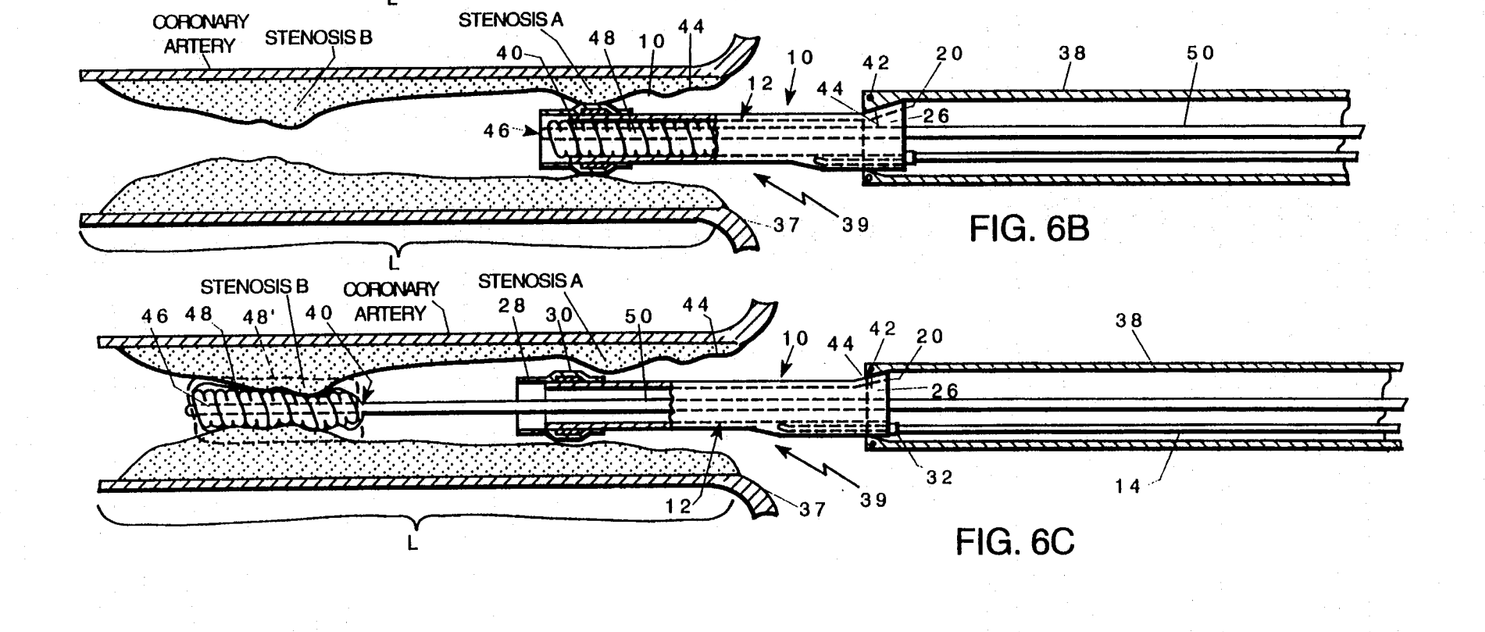

Referring now to FIGS. 6A to 6C, in one procedure for using the present invention, a physician inserts a guide catheter 38 through the aorta 37 and into a patient's coronary ostia 39 using known medical procedures.

The physician then slides a PTCA catheter 40 through L5 the body 12 until the distal tip 46 of the catheter reaches soft tip 28. (See, e.g., FIG. 5.) The balloon 48 of PTCA catheter 40 will then be captured within the confines of body 12. In this arrangement, the relatively fragile PTCA catheter balloon 48 will be safely surrounded by the more durable body 12 during insertion and maneuvering through the guide catheter 38 and vascular system.

Referring specifically to FIG. 6A, the PTCA catheter/support catheter assembly combination then is fed into .guide catheter 38, and advanced through guide catheter 38 to the distal end thereof. Feeding most effectively is accomplished by exerting axial force on wire 14 and on catheter tube 50 simultaneously.

Referring specifically to FIG. 6B, when the PTCA catheter/support catheter assembly combination reaches the distal end of guide catheter 38, it may be advanced as a unit out of the distal end of guide catheter 38, into the coronary ostia 39. Alternatively, support assembly 10 can be advanced first, followed by PTCA catheter 40. Even if, in doing so, PTCA catheter 40 comes out of the proximal end of body 12, funnel portion 26 facilitates reinsertion.

It will be appreciated that body 12 generally will be able to pass further through the coronary ostia than can guide catheter 38 because it is smaller and more maneuverable. Thus, body 12 may be inserted through the ostia and into the coronary artery (see FIG. 14). Even where body 12 cannot reach all the way to a stenotic region which must be opened, e.g., stenosis B in FIGS. 6A to 6C, it will more often than not be able to reach closer to it than can guide catheter 38.

When extending beyond the distal end of guide catheter 38, body 12 functions as a guide catheter extension, and the gap that PTCA catheter 40 must negotiate without assistance is made much shorter. It will be appreciated that this procedure protects the fragile balloon 48 of the PTCA catheter 40 and lessens considerably the tendency of the PTCA catheter 40 to bend, buckle or kink.

In the above procedure, it generally will be preferable that at least some portion of proximal end 20 of body 12 remains within guide catheter 38. To help ensure that proximal end 20 does not unintentionally exit from the guide catheter, the guide catheter may be provided with a marker ring 42 at its distal end. Marker ring 42 preferably is composed of the same radiopaque material as marker band 30 and marker band 32, so that a physician can monitor the relative movement between body 12 and guide catheter 38.

Alternatively, or in addition, guide catheter 38 may be provided with a radially inwardly formed annular ridge 44 for impeding further axial movement of funnel 26 beyond the distal end of guide catheter 38. Of course, since both funnel portion 26 and annular ridge 44 preferably are deformable, should it be necessary to have body 12 pass completely out of guide catheter 38, that can easily be accomplished. However, because of the outward flare of funnel 26 and the inwardly extending ridge 44, that is unlikely to occur accidentally.

As shown in FIG. 6C, after body 12 is positioned adjacent the restricted area, PTCA catheter 40 is advanced so that the balloon 48 exits body 12 and is advanced into the restricted area, e.g., stenosis B, to be opened. Balloon 48 then is inflated, as represented by dotted lines 48', to effect a well known angioplasty procedure. The balloon 48 then is deflated and the PTCA catheter 40, support catheter assembly 10 and guiding catheter 38 may be withdrawn, individually or in combination.

Figure 7:
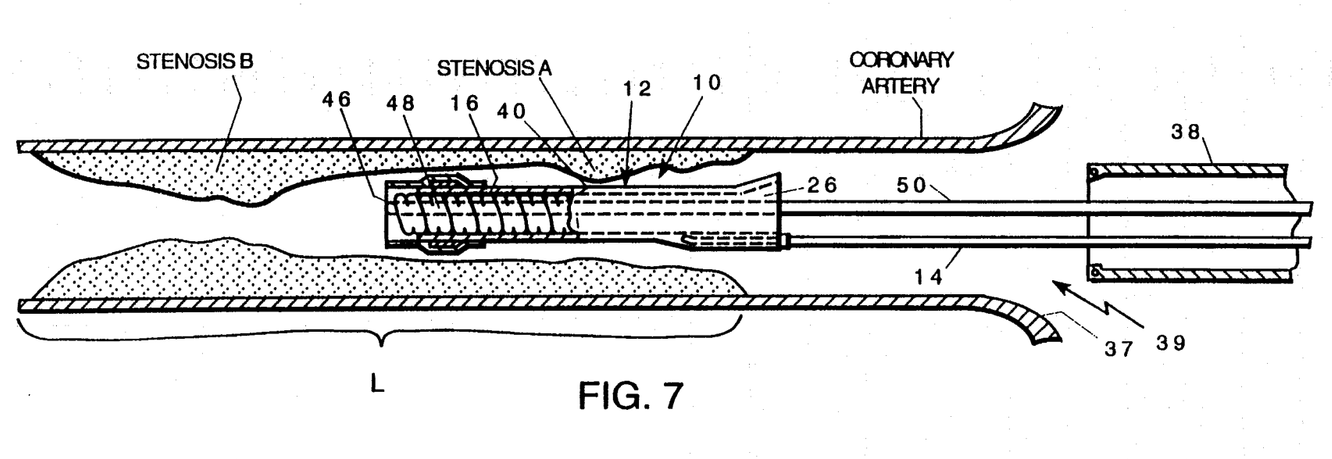
FIG. 7 is a schematic cross-sectional view of a lesion area of a coronary artery having a support catheter of the present invention distally extended from a guide catheter for delivering a PTCA catheter to a restriction in the artery.

FIG. 7 illustrates schematically another procedure in which body 12 is not long enough to reach from the guide catheter to the site where angioplasty is to be performed, e.g., stenosis B. In this case, the bridge body 12/PTCA catheter assembly may be passed completely out of guide catheter 38 and advanced as a unit to the site of the restriction, stenosis B. Angioplasty then may be performed as described above, by passing the PTCA catheter 40 out of the distal end 24 of body 12 into the restriction formed by stenosis B.

Figure 8A:
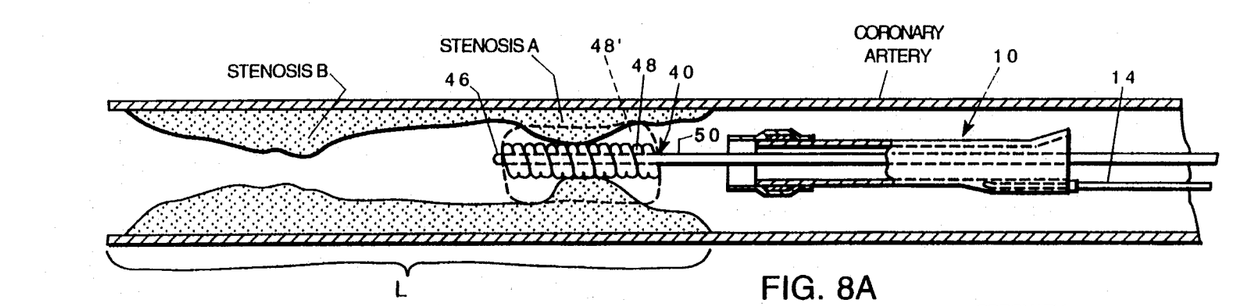
FIGS. 8A to 8C are cross-sectional views showing schematically three stages in a process for guiding a PTCA catheter to a coronary artery lesion, for progressively opening two sequential restrictions in a coronary artery and for disposing a support catheter of the present invention in the opened lesion to inhibit restenosis after withdrawal of the PTCA catheter.
Figure 8B:
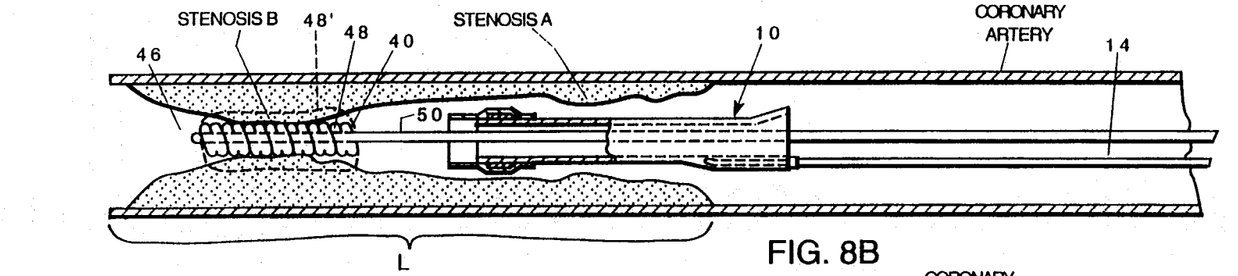

FIGS. 8A to 8C illustrate schematically another procedure for using the present invention, wherein body 12 is used for sequentially reinforcing and advancing a PTCA catheter to two or more stenotic regions. Referring specifically to FIG. 8A, the body/PTCA catheter assembly is advanced to a first restriction site, e.g., stenosis A. PTCA catheter 40 is advanced so that balloon 48 exits the bridge body 12 into the restricted area of stenosis A, and balloon 48 is inflated, as represented by dashed lines 48'. As is well known in the art, inflation of balloon 48 compresses the stenotic walls to increase the size of the lumen therethrough, e.g., to enlarge the cross-section thereof. Balloon 48 then is deflated and PTCA catheter 40 may be advanced to the next restriction site, e.g., stenosis B. As shown in FIG. 8B, the PTCA catheter 40 then is advanced so that balloon 48 is resident in the restricted area of stenosis B, and balloon 48 again is inflated, as represented by dashed lines 48', to open the restricted area.

Of course, after each angioplasty procedure the balloon 48 is deflated so that the PTCA catheter 40 may be advanced. Alternatively, when the balloon 48 is deflated, the mini guide catheter (body 12) may be advanced over the collapsed balloon 48, and then the mini guide catheter/PTCA catheter assembly may be advanced as a single unit. This latter procedure provides protection to the relatively fragile balloon 48 and helps prevent bending, buckling or kinking of the PTCA catheter tube 50 as the PTCA catheter 40 is manipulated through the lesion.

Figure 8C:
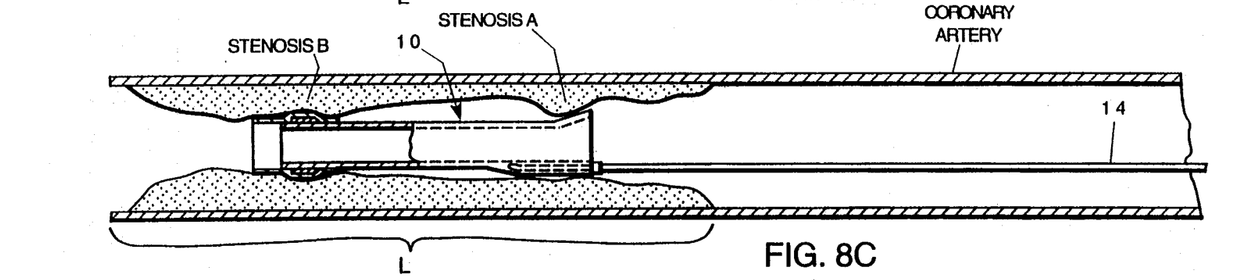

After angioplasty is performed, body 12 may be positioned and retained in the previously restricted stenotic region. For example, FIG. 8B illustrates a procedure wherein body 12 is advanced to reside in the newly enlarged lumen of stenosis A, while the PTCA catheter is advanced to a second restriction site, stenosis B. FIG. 8C illustrates a procedure wherein body 12 is advanced to reside both in the passage opened at stenosis A and the passage subsequently opened at stenosis B, and wherein the PTCA catheter 40 has been withdrawn. In this fashion, body 12 functions as a stent to prevent restenosis of the previously restricted areas, and to maintain an unrestricted flow passage therethrough, e.g., to ensure adequate perfusion of the artery preparatory to surgery.

In yet another procedure for using the present invention, support catheter assembly 10 may be used to facilitate the exchange of one PTCA catheter for another, e.g., for one of a different inflation diameter. In this procedure, a first PTCA catheter is advanced through a patient's vascular system to perform angioplasty using known procedures. When the physician wishes to exchange the first PTCA catheter for a second one, body 12 may be inserted and advanced through the guide catheter and to the newly opened stenosis. The deflated balloon 48 of the first PTCA catheter 40 then may be withdrawn, through body 12, until it exits from guide catheter 38, leaving both the guide catheter and the support catheter assembly in place. The second PTCA catheter then can be inserted. Because of funnel portion 26, the second catheter can negotiate the transition from guide catheter 38 into body 12.

Referring again to FIG. 1, it also may be desirable to provide perforations 64 (shown in phantom) in tube 16 of body 12. Such perforations would facilitate fluid flow through the area by providing greater influx and efflux through lumen 22. This structure also would provide influx and efflux through the wall of body 12 thereby to provide access for blood or other fluids to the cells of the coronary vessel wall or to the plaque formed thereon.

As described in detail above, support catheter assembly 10 may be provided with markers, e.g., radiopaque markers, for subcutaneously detecting the position of body 12 during a medical procedure. Each of the guide catheter 38 and the PTCA catheter 40 also may be provided with one or more markers. Thus, it will be appreciated that a physician, through use of fluoroscopy or some similar technique, will be able to detect both the actual and relative locations of the various devices. More specifically, it will be appreciated that the physician will be able to detect, for example, when a PTCA catheter balloon 48 is captured by, or has fully exited from, body 12.

Although the procedure described above contemplates assembling body 12 and PTCA catheter 40 as a unit before passing them together into guide catheter 38, such preassembly is not necessary. Body 12 could be inserted first, followed by the PTCA catheter 40. As discussed above, funnel portion 26 facilitates passage of the PTCA catheter 40 from the guide catheter 38 into lumen 22 of body 12.

Alternatively, in another procedure the physician may prefer to insert the PTCA catheter 40 first, and use support catheter assembly 10 only when the need for it arises. This may occur, for example, where the physician has inserted a PTCA catheter alone through the guide catheter, only to find that the PTCA catheter cannot negotiate the ostia and coronary artery between the distal end of the guide catheter and the restricted stenotic region. In this case, it may be desirable to provide PTCA catheter 40 with a removable Y-fitting at its proximal end to permit passing body 12 over the PTCA catheter 40 after the latter has been advanced into the guide catheter. Copending U.S. application Ser. No. 07/743,189 discloses a detachable/re-attachable Y-fitting that could be used for this purpose. It will be appreciated that when the Y-fitting is detached, body 12 of the present embodiment will pass easily over the proximal end of PTCA catheter tube 50. The Y-fitting then may be re-attached, and body 12 may be passed down through the guide catheter 38 with the PTCA catheter tube 50 functioning as a guide wire for the body 12.

Figure 9:
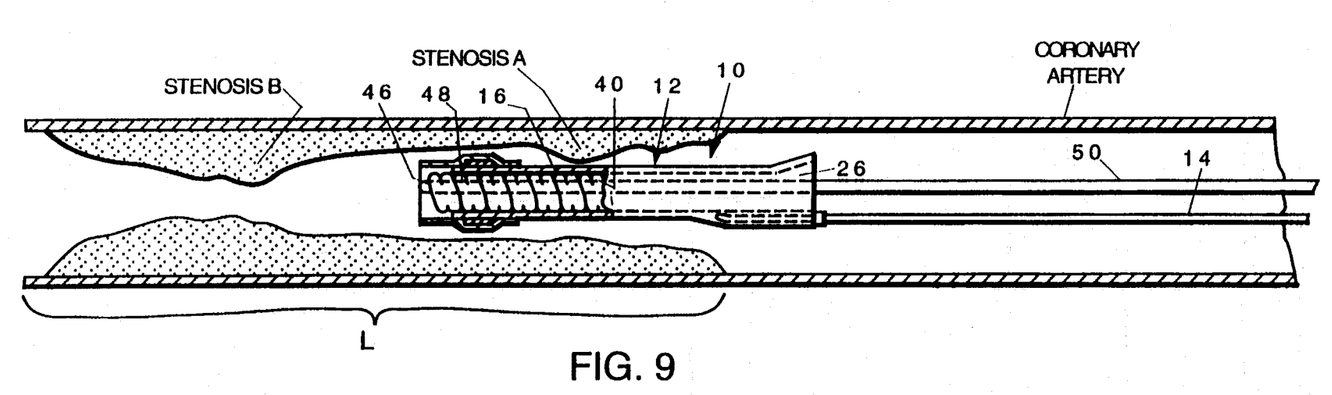
FIG. 9 is a schematic cross-sectional view of a lesion area of a coronary artery having a support catheter of the present invention resident therein for delivering a PTCA catheter to a restriction within the artery.

Although it is believed that the support assembly of the instant invention is most advantageously used in connection with a guide catheter, it may also be used independently. Referring to FIG. 9, the body 12 and PTCA catheter 40 could be assembled as a unit and fed directly into the artery, either percutaneously or by an incision therein. Together, this assembly would then be advanced through the vascular system until it reaches a lesion L, with body 12 acting as a reinforcement to prevent buckling, kinking or bending of the distal end of the catheter.

Figure 10:
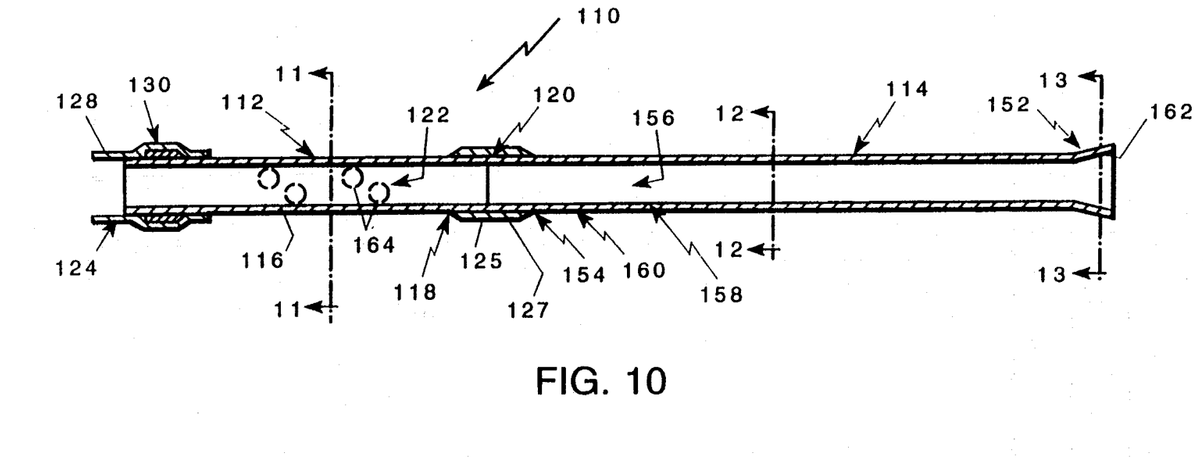
FIG. 10 is a side plan view of a second embodiment of a support catheter of the present invention, cut-away to show in longitudinal cross-section a tubular body having a soft tip and radiopaque marker, and an extension tube having a longitudinal slit therein.

FIGS. 10 to 13 illustrate another embodiment of a support assembly in accordance with the present invention. Referring to FIG. 10, a support assembly 110 is shown cut away in longitudinal cross-section. As in the prior embodiment, support assembly 110 is composed of two major elements: a body 112; and insertion/manipulation means. In this embodiment, the insertion/manipulation means takes the form of a manipulating extension tube. As in the prior embodiment, body 112 includes a body tube 116, a base portion 118 at the proximal end 120 thereof, and a lumen 122 extending therethrough from the proximal end 120 to the distal end 124. Body 112 also may include a soft tip 128 and distal marker band 130, as described in the prior embodiment.

As shown in FIGS. 10 to 13, tube 116 and lumen 122 are generally cylindrical and coaxial along the length of body 112, from proximal end 120 to distal end 124. Body tube 116 is dissimilar to tube 16 of the prior embodiment in that there is no enlarged wall section or flared out funnel at proximal end 120. Instead, base portion 118 is symmetrical about its axis, not eccentric. This symmetrical, generally cylindrical arrangement has a compact structure that, in some circumstances, may provide improved clearance through restricted areas in a blood vessel.

Figure 11:
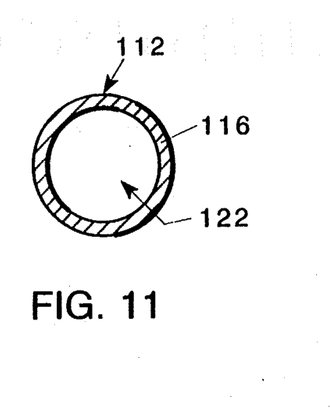
FIG. 11 is a cross-sectional view, taken along line 11—11 of FIG. 10, illustrating a portion of the tubular body of a second embodiment of the invention.
Figure 12:
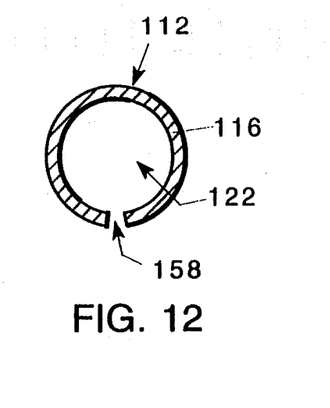
FIG. 12 is a cross-sectional view, taken along line 12—12 of FIG. 10, illustrating a longitudinal slit of the extension tube of a second embodiment of the invention.
Figure 13:
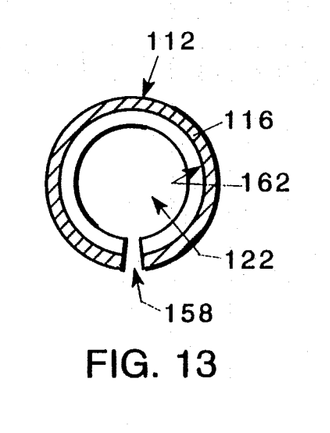
FIG. 13 is a cross-sectional view, taken along line 13—13 of FIG. 10, illustrating a funnel opening of the extension tube of a second embodiment of the invention.

Extension tube 114 extends coaxially from the proximal end 120 of body 112. Extension tube 114 has a proximal end 152, a distal end 154 and a lumen 156 extending therethrough from the proximal end 152 to the distal end 154. As shown in FIGS. 11 and 12, extension tube 114 preferably has the same general cross-section as body tube 116. However, as shown in FIGS. 10 and 12, extension tube 114 also may be provided with a longitudinal slit 158 extending from the proximal end 152 to head portion 160. Referring to FIGS. 10 and 13, extension tube 114 also may be provided with a funnel 162 at its proximal end 152 for facilitating insertion of a catheter, e.g., a PTCA balloon catheter.

As shown in FIG. 10, body tube 116 and extension tube 114 may be joined by a connecting member 125. Connecting member 125 may be an annular ring, and a marker member 127 may be provided therein, similar to marker band 130 in soft tip 128. Alternatively, the proximal end 120 of body tube 116 and the distal end 154 of extension tube 114 could be adhesively bonded. Other means for connecting the two will be readily apparent to those skilled in the art.

The length of the extension tube generally is selected so that the proximal end thereof will remain outside the proximal end of the guide catheter at all times, and therefore may vary depending on the application. In the embodiment shown in FIGS. 11 to 13, extension tube 114 preferably is generally at least about 50 inches long and preferably at least about 53 inches long, and about 0.055 inches in diameter. Preferably, slit 158 is about 45 inches long and 0.005 inches wide. Those skilled in the art will readily be able to select the correct sizing for any given procedure.

The procedures for using the embodiment of FIGS. 10 to 13 generally are the same as the above-described procedures for using the embodiment of FIGS. 1 to 4. In each respective case, the manipulating means (wire 14 or tube 114) provides structure for inserting, manipulating, advancing and withdrawing the body portion (12, 112). In the latter embodiment, the extension tube 114 also provides a funnel portion 162 for facilitating insertion of a catheter therethrough. Thus, this embodiment may provide particular utility where the physician knows it will be necessary to use several catheters sequentially, e.g., several PTCA balloon catheters having different inflation sizes. Specifically, since the physician has the entry to the bridge tube 116 (i.e., proximal end 152) in hand, it is not necessary to search for it near the distal end 24 of the guide catheter 38.

As noted above, extension tube 114 is provided with a slit 158 extending longitudinally from the proximal end 152 to head portion 160. The slit 152 allows the physician to use the assembly 110 with a catheter that has already been inserted, without first removing the catheter. For example, when used with the above-noted Y-fitted PTCA catheter disclosed in co-pending U.S. application Ser. No. 07/743,189, the physician may insert the PTCA catheter through the guide catheter 38 and, if unsuccessful in attempting to pass it unaided into a restriction, the detachable fitting or adaptor can be removed. Assembly 110 then can be passed over the PTCA catheter tube 50 until the proximal end of the PTCA catheter passes through body 112 and head portion 160 of extension tube 114, and reaches slit 158. The proximal end of the PTCA catheter tube 50 then is passed out through the slit 158 and is held in place by the physician. It will be appreciated that the physician then can advance the assembly 110 by pushing on the extension tube 114 while progressively pressing catheter tube 50 through slit 158 into lumen 122. In this procedure, the physician maintains control over the PTCA catheter at all times.

Of course, the device of the present invention may be used with almost any type of catheter, including over-the-wire catheters as well as catheters with captive guide wires.

It will be appreciated that the above described embodiments and procedures are illustrative only. Numerous other features, advantages, equivalent structures, procedures and modifications of the present invention readily will come to mind among those skilled in the art. Accordingly, the present invention is not limited to the above-described embodiments, but is intended to include all structures and procedures that come within the scope of the following claims, and all equivalents thereto.

What is claimed is:

1. An angioplasty device for use in a vascular procedure in which a balloon dilatation catheter is advanced by a physician into the vasculature of a patient through a previously inserted guiding catheter and beyond the distal end of the guiding catheter into a coronary artery of the patient to the region of a stenotic lesion to be dilated, said device comprising:

a tubular body having a base portion disposed at a proximal end thereof, and having a continuous lumen therethrough from a proximal end to a distal end thereof, said lumen having a cross-section and a length, the cross-section of said lumen being large enough to permit passage therethrough of a balloon of the balloon dilatation catheter, said tubular body being configured to be advanced over the balloon dilatation catheter and to pass through the guiding catheter to the region of the coronary lesion; and a proximal member connected to said tubular body and extending proximally therefrom for providing communication between said tubular body and a region outside of the body of the patient;

wherein said tubular body is further constructed and arranged to be advanced beyond the distal end of the guiding catheter, inserted into a dilated area of the stenotic lesion and maintained in place to inhibit restenosis of the region.

2. A device as recited in claim 1, wherein said device is constructed and arranged to remain in the region of the lesion while the balloon catheter is withdrawn, to facilitate the exchange of one dilatation balloon catheter for another.

3. A device as recited in claim 1, wherein the base portion of said body has an eccentric cross-section.

4. A device as recited in claim 1, wherein said tubular body is constructed and arranged to provide a blood flow passage to the dilated area of the stenotic lesion.

5. A device as recited in claim 4, wherein said device is constructed and arranged so that said tubular body extends outside of the distal end of the guiding catheter, while said tubular body is within the dilated area of the stenotic lesion, said tubular body thereby maintaining a substantially unrestricted blood flow passage through the dilated area.

6. A device as recited in claim 1, wherein said proximal member is a manipulation wire.

7. A device as recited in claim 1, wherein said tubular body is sized so that the physician can hold the proximal portion of the dilatation catheter at a location spaced from the proximal end of the dilatation catheter while said tubular member is being advanced over the proximal end of the dilatation catheter and so that the physician can hold the proximal end of the dilatation catheter once the proximal portion of said tubular body has advanced over the proximal end of the dilatation catheter, thereby enabling the physician to maintain control of the dilatation catheter at all times during the PTCA procedure.

8. A device as recited in claim 7, wherein the length of said lumen is at least as long as the length of the balloon of the dilatation catheter.

9. A device as recited in claim 7, wherein the length of said lumen is at least eight times as long as the length of the balloon of the dilatation catheter.

10. A device as recited in claim 7, wherein said body is about 12 inches long.

11. A device as recited in claim 1, wherein said body is at least about twelve inches long.

12. A device as recited in claim 1, wherein said proximal member is at least about 50 inches long.

13. A device as recited in claim 1, further comprising a tip member disposed at the distal end of said body wherein said tip member is soft and flexible.

14. A device as recited in claim 13, wherein said tip member is composed of a copolymer of polyethylene and ethylvinylalcohol.

15. A device as recited in claim 1, further comprising marker means for detecting the location of said body during the vascular procedure.

16. A device as recited in claim 1, wherein the wall portions of said tubular body have perforations for facilitating fluid flow to the area of the stenotic lesion.

17. The device recited in claim 1 wherein said tubular body includes an enlarged opening at the proximal end thereof.

18. The device as recited in claim 17, wherein the enlarged opening is funnel-shaped.

19. An angioplasty device for use in a vascular procedure in which a balloon dilatation catheter is advanced by a physician into the vasculature of a patient through a previously inserted guiding catheter and beyond the distal end of the guiding catheter into a coronary artery of the patient to the region of a stenotic lesion to be dilated, said device comprising:

a tubular body having a base portion disposed at a proximal end thereof, and having a continuous lumen therethrough from a proximal end to a distal end thereof, said lumen having a cross-section and a length, the cross-section of said lumen being large enough to permit passage therethrough of a balloon of the balloon dilatation catheter, said tubular body being short relative to the balloon catheter and being configured to be advanced over the balloon dilatation catheter and to pass through the guiding catheter to the region of the lesion, said device being constructed to permit the physician to maintain control of the dilatation catheter at all times during the PTCA procedure; and a proximal member that is thin relative to said tubular body and is connected to said tubular body and extends proximally therefrom for providing communication between said tubular body and a region outside of the body of the patient, wherein said tubular body is further sized and constructed to be inserted into a dilated area of the stenotic lesion and maintained in place to inhibit restenosis of the lesion.

20. A device as recited in claim 19, wherein said device is constructed and arranged to remain in the region of the lesion while the balloon catheter is withdrawn.

21. A device as recited in claim 19, wherein said device is constructed and arranged so that a proximal portion of said tubular body remains within the guiding catheter while said tubular body extends to the region of the lesion.

22. A device as recited in claim 19, wherein said proximal member is constructed and arranged to facilitate insertion of said tubular body to the region of the stenotic lesion.

23. A device as recited in claim 19, wherein said proximal member is a manipulation wire.

24. The device of claim 1 wherein said device is constructed to permit the physician to maintain control of the dilatation catheter at all times during the vascular procedure.

25. The device of claim 19 further sized and constructed to be advanced beyond the distal end of the guiding catheter and into the dilated region.

26. A method for treating a patient having a restricted stenotic region in a coronary artery, said method comprising the steps of:

inserting into the patient a guiding catheter having a distal end and positioning the guiding catheter so that the distal end of the guiding catheter is positioned in the vicinity of the ostium of the patient;

inserting a PTCA balloon catheter through the guiding catheter to the vicinity of the restricted region of the patient's coronary artery;

dilating the restricted stenotic region with the PTCA balloon catheter;

inserting a device beyond the distal end of the guiding catheter and into a selected site in the dilated region of the coronary artery to prevent restenosis of the dilated region at that site, said device comprising a tubular body having a base portion disposed at a proximal end thereof, and having a continuous lumen therethrough from a proximal end to a distal end thereof, said lumen having a cross-section and a length, the cross-section of said lumen being large enough to permit passage therethrough of the balloon of the balloon dilatation catheter, said tubular body being short relative to the balloon catheter and being configured to be advanced over the balloon dilatation catheter and to pass through the guiding catheter to the region of the lesion, said device being constructed to permit the physician to maintain control of the dilatation catheter at all times during the PTCA procedure, and a proximal member that is thin relative to said tubular body and is connected to said tubular body and extends proximally therefrom for providing communication between said tubular body and a region outside of the body of the patient.

27. The method of claim 26 wherein said device is inserted through said guiding catheter over said PTCA balloon catheter.

28. The method of claim 26 wherein, prior to dilation of the restricted stenotic region, at least the balloon of said PTCA balloon catheter is disposed within the tubular body of said device and said balloon catheter and said device are advanced as a unit through said guiding catheter and beyond the distal end of said guiding catheter to the vicinity of the stenotic region of the patient's coronary artery.

29. The method of claim 28 wherein said stenotic region is dilated by advancing the balloon of said PTCA balloon catheter beyond the distal end of the tubular body of said device and into the stenotic region, and by expanding the balloon once the balloon is positioned in a selected site in the stenotic region.

30. The method of claim 29 further comprising the steps of withdrawing said PTCA balloon catheter from the dilated region, and leaving the tubular body of said device positioned in the stenotic region to prevent restenosis of the previously restricted region and to maintain an unrestricted flow passage therethrough.

31. The method of claim 30 further comprising the step of withdrawing said guiding catheter from the patient.

32. The method of claim 26 wherein said proximal member of the device that is inserted into the patient is constructed and arranged to facilitate insertion of said tubular body to the region of the stenotic lesion.

33. The method of claim 32 wherein the proximal member of the device that is inserted into the patient is a manipulation wire.

* * * * *